(12) United States Patent
Lewis et al.

(10) Patent No.: US 8,696,886 B1
(45) Date of Patent: Apr. 15, 2014

(54) SILICOMETALLOPHOSPHATE MOLECULAR SIEVES, METHOD OF PREPARATION AND USE

(71) Applicant: UOP LLC, Des Plaines, IL (US)

(72) Inventors: Gregory J. Lewis, Santa Cruz, CA (US); Lisa M. Knight, Chicago, IL (US); Paulina Jakubczak, Elk Grove Village, IL (US); Justin E. Stanczyk, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/054,980

(22) Filed: Oct. 16, 2013

Related U.S. Application Data

(62) Division of application No. 13/689,893, filed on Nov. 30, 2012, now Pat. No. 8,569,557.

(51) Int. Cl.
*C10G 47/16* (2006.01)
*C10G 47/20* (2006.01)

(52) U.S. Cl.
USPC ............ 208/109; 208/111.01; 208/111.25; 208/111.35; 208/111.05

(58) Field of Classification Search
USPC ............ 208/109, 111.01, 111.25, 111.35, 208/111.05
See application file for complete search history.

(56) References Cited

U.S. PATENT DOCUMENTS 4,973,785 A * 11/1990 Lok et al. .............. 585/481

\* cited by examiner

*Primary Examiner* — Thuan D Dang
(74) *Attorney, Agent, or Firm* — Maryann Maas

(57) ABSTRACT

A new family of crystalline microporous silicometallophosphates designated MAPSO-64 and modified forms thereof have been synthesized. These silicometallophosphates are represented by the empirical formula $R^+_r M_m^{2+} E P_x Si_y O_z$ where R is an organoammonium cation such as ETMA$^+$ or DEDMA$^+$, M is an alkaline earth or transition metal cation of valence 2+, and E is a trivalent framework element such as aluminum or gallium. The MAPSO-64 compositions are characterized by a BPH framework topology and have catalytic properties for carrying out various hydrocarbon conversion processes, and separation properties for separating at least one component.

11 Claims, No Drawings

SILICOMETALLOPHOSPHATE MOLECULAR SIEVES, METHOD OF PREPARATION AND USE

CROSS-REFERENCE TO RELATED APPLICATION

This application is a Division of copending application Ser. No. 13/689,893 filed Nov. 30, 2012, the contents of which are hereby incorporated by reference in its entirety.

FIELD OF THE INVENTION

This invention relates to a new family of charged silicometallophosphate-based molecular sieves designated MAPSO-64 as the catalytic composite for hydrocarbon conversion reactions, or as a separation material used in separation processes. They are represented by the empirical formula of:

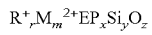

where M is a divalent framework metal such as magnesium or zinc, R is an organoammonium cation such as ethyltrimethylammonium or diethyldimethylammonium and E is a trivalent framework element such as aluminum or gallium.

BACKGROUND OF THE INVENTION

Zeolites are crystalline aluminosilicate compositions which are microporous and which are formed from corner sharing $AlO_2^-$ and $SiO_2$ tetrahedra. Numerous zeolites, both naturally occurring and synthetically prepared are used in various industrial processes. Synthetic zeolites are prepared via hydrothermal synthesis employing suitable sources of Si, Al and structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Zeolites can be used as catalysts for hydrocarbon conversion reactions, which can take place on outside surfaces of the zeolite as well as on internal surfaces within the pores of the zeolite.

In 1982, Wilson et al. developed aluminophosphate molecular sieves, the so-called AlPOs, which are microporous materials that have many of the same properties of zeolites, but are silica free, composed of $AlO_2^-$ and $PO_2^+$ tetrahedra, see U.S. Pat. No. 4,310,440. Subsequently, charge was introduced to the neutral aluminophosphate frameworks via the substitution of $SiO_2$ tetrahedra for $PO_2^+$ tetrahedra to produce the SAPO molecular sieves, see U.S. Pat. No. 4,440,871. Another way to introduce framework charge to neutral aluminophosphates is to substitute $[M^{2+}O_2]^{2-}$ tetrahedra for $AlO_2^-$ tetrahedra, which yield the MeAPO molecular sieves, see U.S. Pat. No. 4,567,029. It is furthermore possible to introduce framework charge on AlPO-based molecular sieves via the introduction of both $SiO_2$ and $[M^{2+}O_2]^{2-}$ tetrahedra to the framework, giving MeAPSO molecular sieves, see U.S. Pat. No. 4,973,785.

Applicants have synthesized a new family of charged microporous silicometallophosphate framework materials with MeAPSO compositions designated MAPSO-64. The MAPSO-64 materials have the BPH topology, which contains a 12-ring pore system with a perpendicular 8-ring pore system, see http://izasc-mirror.la.asu.edu/fmi/xsl/IZA-SC/ftc_fw.xsl?-db=Atlas_main&-lay=fw&-max=25&STC=BPH&-find. With respect to AlPO-based materials, the BPH topology has previously been prepared in a MAPO composition of the material known as STA-5, which uses the complicated triquat template 1,3,5-Tris(triethylammoniomethyl)benzene, see Patinec et. al. in *Chem. Mater.*, 11, 2456-2462 (1999). By contrast, the microporous MAPSO-64 materials of the present invention additionally include Si in the framework and can be prepared with the much simpler structure directing agents diethyldimethylammonium ($DEDMA^+$) or ethyltrimethylammonium ($ETMA^+$).

SUMMARY OF THE INVENTION

As stated, the present invention relates to a new family of microporous silicometallophosphate molecular sieves designated MAPSO-64. One embodiment of the invention is a microporous crystalline material having a three-dimensional framework of containing $EO_2^-$, $PO_2^+$, $[M^{2+}O_2]^{2-}$ and $SiO_2$ tetrahedral units and an empirical composition in the as synthesized and anhydrous basis expressed by an empirical formula of:

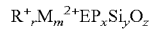

where M is at least one framework divalent metal cation selected from the group consisting of $Be^{2+}$, $Mg^{2+}$, $Zn^{2+}$, $Co^{2+}$, $Mn^{2+}$, $Fe^{2+}$, $Ni^{2+}$, "m" is the mole ratio of M to E and varies from 0.01 to about 1.5, R is an organoammonium cation selected from the group consisting of tetramethylammonium ($TMA^+$), ethyltrimethylammonium ($ETMA^+$), diethyldimethylammonium ($DEDMA^+$), choline, propyltrimethylammonium ($PTMA^+$), methyltriethylammonium ($MTEA^+$), tetraethylammonium ($TEA^+$), dimethyldipropylammonium ($DPDMA^+$), tetrapropylammonium ($TPA^+$) and mixtures thereof, "r" is the mole ratio of R to E and has a value of about 0.1 to about 2.0, E is an trivalent element selected from the group consisting of aluminum, gallium, iron, boron and mixtures thereof, "x" is mole ratio of P to E and varies from 0.5 to about 2.5, "y" is the mole ratio of Si to E and varies from 0.01 to about 1.0, and "z" is the mole ratio of O to E and has a value determined by the equation:

$$z=(2 \cdot m+r+3+5 \cdot x+4 \cdot y)/2$$

and is characterized in that it has the x-ray diffraction pattern having at least the d-spacings and intensities set forth in Table A:

TABLE A

| 2Θ | d(Å) | I/I$_0$ |
|---|---|---|
| 6.81-6.61 | 12.98-13.34 | m-vs |
| 7.75-7.55 | 11.40-11.70 | m-vs |
| 13.36-13.14 | 6.62-6.73 | w-m |
| 13.51-13.32 | 6.55-6.64 | w-m |
| 14.98-14.68 | 5.91-6.03 | w |
| 15.51-15.34 | 5.71-5.77 | w-m |
| 18.99-18.79 | 4.67-4.72 | w-m |
| 20.26-20.07 | 4.38-4.42 | w-m |
| 21.50-21.24 | 4.13-4.18 | w-s |
| 24.10-23.84 | 3.69-3.73 | w-m |
| 24.30-24.03 | 3.66-3.70 | w-m |
| 24.57-24.23 | 3.62-3.67 | w-m |

TABLE A-continued

| 2Θ | d(Å) | I/I₀ |
|---|---|---|
| 26.83-26.51 | 3.32-3.36 | w-m |
| 27.59-27.42 | 3.23-3.25 | w-m |
| 27.86-27.59 | 3.20-3.23 | w |
| 28.68-28.49 | 3.11-3.13 | w |
| 28.87-28.59 | 3.09-3.12 | w |
| 30.06-29.76 | 2.97-3.00 | w-m |
| 30.27-29.96 | 2.95-2.98 | w-m |
| 31.03-30.70 | 2.88-2.91 | w-m |
| 33.80-33.54 | 2.65-2.67 | w-m |
| 34.06-33.80 | 2.63-2.65 | w |
| 35.60-35.31 | 2.52-2.54 | w-m |
| 36.65-36.34 | 2.45-2.47 | w |
| 38.44-38.10 | 2.34-2.36 | w |

Another embodiment of the invention is a process for preparing the crystalline microporous aluminum phosphate-based molecular sieve described above. The process comprises forming a reaction mixture containing reactive sources of R, E, P, and either one or both of M and Si and heating the reaction mixture at a temperature of about 60° C. to about 200° C. for a time sufficient to form the molecular sieve, the reaction mixture having a composition expressed in terms of mole ratios of the oxides of:

$$aR_2O:bMO:E_2O_3:cP_2O_5:dSiO_2:eH_2O$$

where "a" has a value of about 0.75 to about 16, "b" has a value of about 0.01 to about 3, "c" has a value of about 0.8 to about 8, "d" has a value of about 0.01 to about 4, and "e" has a value from 20 to 800.

Yet another embodiment of the invention is a hydrocarbon conversion process using the above-described molecular sieve as a catalyst. The process comprises contacting at least one hydrocarbon with the molecular sieve at conversion conditions to generate at least one converted hydrocarbon.

Still another embodiment of the invention is a separation process using the crystalline MAPSO-64 material. The process may involve separating mixtures of molecular species or removing contaminants by contacting a fluid with the MAPSO-64 molecular sieve. Separation of molecular species can be based either on the molecular size (kinetic diameter) or on the degree of polarity of the molecular species. Removing contaminants may be by ion exchange with the molecular sieve.

DETAILED DESCRIPTION OF THE INVENTION

Applicants have prepared a family of microporous silicometallophosphate materials whose structures exhibit the BPH topology and are useful as at least a portion of the catalyst composite in hydrocarbon conversion reactions and are also useful in separation processes to separate at least one component from at least one other component. The instant microporous crystalline material (MAPSO-64) has an empirical composition in the as-synthesized form and on an anhydrous basis expressed by the empirical formula:

$$R^+_r M_m^{2+} E P_x Si_y O_z$$

where M is at least one divalent metal cation and is selected from the group consisting of alkaline earth and transition metals. Specific examples of the M cations include but are not limited to beryllium, magnesium, cobalt (II), manganese, zinc, iron(II), nickel and mixtures thereof. R is an organoammonium cation, examples of which include but are not limited to the choline cation, $[(CH_3)_3N(CH_2)_2OH]^+$, tetramethylammonium cation (TMA$^+$), ethyltrimethylammonium (ETMA$^+$), trimethylpropylammonium, diethyldimethylammonium (DEDMA$^+$), methyltriethylammonium (MTEA$^+$), trimethylpropylammonium (PTMA$^+$), dimethyldiethanolammonium, tetraethylammonium (TEA$^+$), dimethyldipropylammonium (DPDMA$^+$), tetrapropylammonium (TPA$^+$) and mixtures thereof and "r" is the mole ratio of R to E and varies from about 0.1 to about 2.0. The value of "m" is the mole ratio of M to E and varies from 0.01 to about 1.5, "x" is mole ratio of P to E and varies from 0.5 to about 2.5. The ratio of silicon to E is represented by "y" which varies from about 0.01 to about 1.0. E is a trivalent element which is tetrahedrally coordinated, is present in the framework and is selected from the group consisting of aluminum, gallium, iron(III) and boron. Lastly, "z" is the mole ratio of O to E and is given by the equation:

$$z=(2\cdot m+r+3+5\cdot x+4\cdot y)/2.$$

The microporous crystalline silicometallophosphate material, MAPSO-64, is prepared by a hydrothermal crystallization of a reaction mixture prepared by combining reactive sources of R, E, phosphorous, M and silicon. When E is aluminum, the sources of include but are not limited to aluminum alkoxides, precipitated aluminas, aluminum metal, aluminum hydroxide, aluminum salts and alumina sols. Specific examples of aluminum alkoxides include, but are not limited to aluminum ortho sec-butoxide and aluminum ortho isopropoxide. Sources of other E elements include but are not limited to organoammonium borates, boric acid, precipitated gallium oxyhydroxide, gallium sulfate, ferric sulfate, and ferric chloride. Sources of phosphorus include, but are not limited to, orthophosphoric acid, phosphorus pentoxide, and ammonium dihydrogen phosphate. Sources of silica include but are not limited to tetraethylorthosilicate, colloidal silica, and precipitated silica. Sources of the M metals include the halide salts, nitrate salts, acetate salts, and sulfate salts of the respective alkaline earth and transition metals. R is an organoammonium cation selected from the group consisting of choline, TMA$^+$, ETMA$^+$, DEDMA$^+$, MTEA$^+$, TEA$^+$, TPA$^+$, PTMA$^+$, DPDMA$^+$, dimethyldiethanolammonium and mixtures thereof, and the sources include the hydroxide, chloride, bromide, iodide and fluoride compounds. Specific examples include without limitation choline hydroxide and choline chloride, ethyltrimethylammonium hydroxide, diethyldimethylammonium hydroxide, diethyldimethylammonium chloride, methyltriethylammonium hydroxide, and methyltriethylammonium chloride. In a specific embodiment, R is DEDMA$^+$. In another embodiment, R is at ETMA$^+$. In another embodiment, R is a combination of DEDMA$^+$ and at least one singly charged organoammonium cation selected from the group consisting of choline, TMA$^+$, ETMA$^+$, MTEA$^+$, PTMA$^+$, dimethyldiethanolammonium, TEA$^+$, DPDMA$^+$ and TPA$^+$. In yet another embodiment, R is a combination of ETMA$^+$ and at least one singly charged organoammonium cation selected from the group consisting of choline, TMA$^+$, DEDMA$^+$, MTEA$^+$, PTMA$^+$, DPDMA$^+$, dimethyldiethanolammonium, TEA$^+$, and TPA$^+$.

The reaction mixture containing reactive sources of the desired components can be described in terms of molar ratios of the oxides by the formula:

$$aR_2O:bMO:E_2O_3:cP_2O_5:dSiO_2:eH_2O$$

where "a" varies from about 0.75 to about 16, "b" varies from about 0.01 to about 3, "c" varies from about 0.8 to about 8, "d" varies from about 0 to about 4, and "e" varies from 20 to 800. If alkoxides are used, a distillation or evaporative step may be included to remove the alcohol hydrolysis products. The reaction mixture is now reacted at a temperature of about 60° C. to about 200° C., and in another embodiment from about 115° C.

to about 175° C. for a period of about 1 day to about 3 weeks and in another embodiment, for a time of about 1 day to about 7 days in a sealed reaction vessel under autogenous pressure. After crystallization is complete, the solid product is isolated from the heterogeneous mixture by means such as filtration or centrifugation, and then washed with deionized water and dried in air at ambient temperature up to about 100° C. MAPSO-64 seeds can optionally be added to the reaction mixture in order to accelerate the formation of the desired microporous composition.

The MAPSO-64 silicometallophosphate-based material, which is obtained from the above-described process, is characterized by the x-ray diffraction pattern, having at least the d-spacings and relative intensities set forth in Table A below.

TABLE A

| 2Θ | d(Å) | I/I₀ |
|---|---|---|
| 6.81-6.61 | 12.98-13.34 | m-vs |
| 7.75-7.55 | 11.40-11.70 | m-vs |
| 13.36-13.14 | 6.62-6.73 | w-m |
| 13.51-13.32 | 6.55-6.64 | w-m |
| 14.98-14.68 | 5.91-6.03 | w |
| 15.51-15.34 | 5.71-5.77 | w-m |
| 18.99-18.79 | 4.67-4.72 | w-m |
| 20.26-20.07 | 4.38-4.42 | w-m |
| 21.50-21.24 | 4.13-4.18 | w-s |
| 24.10-23.84 | 3.69-3.73 | w-m |
| 24.30-24.03 | 3.66-3.70 | w-m |
| 24.57-24.23 | 3.62-3.67 | w-m |
| 26.83-26.51 | 3.32-3.36 | w-m |
| 27.59-27.42 | 3.23-3.25 | w-m |
| 27.86-27.59 | 3.20-3.23 | w |
| 28.68-28.49 | 3.11-3.13 | w |
| 28.87-28.59 | 3.09-3.12 | w |
| 30.06-29.76 | 2.97-3.00 | w-m |
| 30.27-29.96 | 2.95-2.98 | w-m |
| 31.03-30.70 | 2.88-2.91 | w-m |
| 33.80-33.54 | 2.65-2.67 | w-m |
| 34.06-33.80 | 2.63-2.65 | w |
| 35.60-35.31 | 2.52-2.54 | w-m |
| 36.65-36.34 | 2.45-2.47 | w |
| 38.44-38.10 | 2.34-2.36 | w |

The MAPSO-64 may be modified in many ways to tailor it for use in a particular application. Modifications include calcination, ammonia calcinations, ion-exchange, steaming, various acid extractions, ammonium hexafluorosilicate treatment, or any combination thereof, as outlined for the case of UZM-4 in U.S. Pat. No. 6,776,975 B1 which is incorporated by reference in its entirety. Properties that may be modified include porosity, adsorption, framework composition, acidity, thermal stability, etc.

As synthesized, the MAPSO-64 material will contain some of the exchangeable or charge balancing cations in its pores. These exchangeable cations can be exchanged for other cations, or in the case of organic cations, they can be removed by heating under controlled conditions. With the large 12-ring pore BPH topology of MAPSO-64, small organoammonium cations can often be removed directly by ion-exchange. In one embodiment, the method of removing organic cations from the pores is ammonia calcination. Calcination in air converts organic cations in the pores to protons, which can, for example, lead to some removal of Al from the framework upon exposure to water vapor. When the calcination is carried out in an ammonia atmosphere, the organic cation in the pore is replaced by $NH_4^+$ cation and the framework remains intact, see Studies in Surface Science, (004) vol. 154, p. 1324-1331. Typical conditions for ammonia calcinations include the use of gaseous anhydrous ammonia flowing at a rate of 1.1 l/min while ramping the sample at 2-5° C./min to 500° C. and holding at that temperature for a time ranging from 5 minutes to 4 hours. The resulting ammonium form of MAPSO-64 has essentially the diffraction pattern of Table A. The ammonium form of MAPSO-64 may then be ion-exchanged to any other form, resulting in a material with a modified composition, MAPSO-64M, given by the empirical formula:

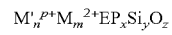

where M is at least one divalent metal cation selected from the group consisting of $Be^{2+}$, $Mg^{2+}$, $Zn^{2+}$, $Co^{2+}$, $Mn^{2+}$, $Fe^{2+}$, $Ni^{2+}$, "m" is the mole ratio of M to E and varies from 0.01 to about 1.5, M' is $NH_4^+$, $H^+$, alkali metals, alkaline earth metals, transition metals and rare earth metals and mixtures thereof, "n" is the mole ratio of M' to E and has a value of about 0.03 to about 2.0, "p" is the weighted average valence of M', E is a trivalent element selected from the group consisting of aluminum, gallium, iron, boron and mixtures thereof, "x" is mole ratio of P to E and varies from 0.5 to about 2.0, "y" is the mole ratio of Si to E and varies from 0.01 to about 1.0 and "z" is the mole ratio of O to E and has a value determined by the equation:

$$z=(p \cdot n+2 \cdot m+3+5 \cdot x+4 \cdot y)/2$$

and is characterized in that it has the x-ray diffraction pattern having at least the d-spacings and intensities set forth in Table A:

TABLE A

| 2Θ | d(Å) | I/I₀ |
|---|---|---|
| 6.81-6.61 | 12.98-13.34 | m-vs |
| 7.75-7.55 | 11.40-11.70 | m-vs |
| 13.36-13.14 | 6.62-6.73 | w-m |
| 13.51-13.32 | 6.55-6.64 | w-m |
| 14.98-14.68 | 5.91-6.03 | w |
| 15.51-15.34 | 5.71-5.77 | w-m |
| 18.99-18.79 | 4.67-4.72 | w-m |
| 20.26-20.07 | 4.38-4.42 | w-m |
| 21.50-21.24 | 4.13-4.18 | w-s |
| 24.10-23.84 | 3.69-3.73 | w-m |
| 24.30-24.03 | 3.66-3.70 | w-m |
| 24.57-24.23 | 3.62-3.67 | w-m |
| 26.83-26.51 | 3.32-3.36 | w-m |
| 27.59-27.42 | 3.23-3.25 | w-m |
| 27.86-27.59 | 3.20-3.23 | w |
| 28.68-28.49 | 3.11-3.13 | w |
| 28.87-28.59 | 3.09-3.12 | w |
| 30.06-29.76 | 2.97-3.00 | w-m |
| 30.27-29.96 | 2.95-2.98 | w-m |
| 31.03-30.70 | 2.88-2.91 | w-m |
| 33.80-33.54 | 2.65-2.67 | w-m |
| 34.06-33.80 | 2.63-2.65 | w |
| 35.60-35.31 | 2.52-2.54 | w-m |
| 36.65-36.34 | 2.45-2.47 | w |
| 38.44-38.10 | 2.34-2.36 | w |

In one embodiment of the invention, the MAPSO-64 is thermally stable up to a temperature of at least 400° C., and in another embodiment the MAPSO-64 is thermally stable up to a temperature of at least 500° C.

When MAPSO-64 is calcined in air and ambient water vapor, there can be loss of metal from the framework, such as Al, which can alter the x-ray diffraction pattern from that observed for the as-synthesized MAPSO-64 in Table A, see Studies in Surface Science, (2004) vol. 154, p. 1324-1331. The air-calcined MAPSO-64 materials, MAPSO-64C, are characterized by the empirical formula:

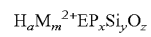

where M is at least one divalent metal cation selected from the group consisting of $Be^{2+}$, $Mg^{2+}$, $Zn^{2+}$, $Co^{2+}$, $Mn^{2+}$, $Fe^{2+}$, Ni$^{2+}$, "m" is the mole ratio of M to E and varies from 0.01 to about 1.5, H is a proton, "a" is the mole ratio of H to E and has a value of about 0.1 to about 2.0, E is a trivalent element selected from the group consisting of aluminum, gallium, iron, boron and mixtures thereof, "x" is mole ratio of P to E and varies from 0.5 to about 2.5, "y" is the mole ratio of Si to E and varies from 0.01 to about 1.0 and "z" is the mole ratio of O to E and has a value determined by the equation:

$$z=(a+2 \cdot m+3+5 \cdot x+4 \cdot y)/2$$

The crystalline MAPSO-64 material of this invention can be used for separating mixtures of molecular species, removing contaminants through ion exchange and catalyzing various hydrocarbon conversion processes. Separation of molecular species can be based either on the molecular size (kinetic diameter) or on the degree of polarity of the molecular species.

The MAPSO-64 compositions of this invention can also be used as a catalyst or catalyst support in various hydrocarbon conversion processes. Hydrocarbon conversion processes are well known in the art and include cracking, hydrocracking, alkylation of both aromatics and isoparaffin, isomerization, polymerization, reforming, hydrogenation, dehydrogenation, transalkylation, dealkylation, hydration, dehydration, hydrotreating, hydrodenitrogenation, hydrodesulfurization, methanol to olefins, methanation and syngas shift process. Specific reaction conditions and the types of feeds which can be used in these processes are set forth in U.S. Pat. No. 4,310,440, U.S. Pat. No. 4,440,871 and U.S. Pat. No. 5,126,308, which are hereby incorporated by reference. Preferred hydrocarbon conversion processes are those in which hydrogen is a component such as hydrotreating or hydrofining, hydrogenation, hydrocracking, hydrodenitrogenation, hydrodesulfurization, etc.

Hydrocracking conditions typically include a temperature in the range of 400° to 1200° F. (204-649° C.), preferably between 600° and 950° F. (316-510° C.). Reaction pressures are in the range of atmospheric to about 3,500 psig (24,132 kPa g), preferably between 200 and 3000 psig (1379-20,685 kPa g). Contact times usually correspond to liquid hourly space velocities (LHSV) in the range of about 0.1 hr$^{-1}$ to 15 hr$^{-1}$, preferably between about 0.2 and 3 hr$^{-1}$. Hydrogen circulation rates are in the range of 1,000 to 50,000 standard cubic feet (scf) per barrel of charge (178-8,888 std. m$^3$/m$^3$), preferably between 2,000 and 30,000 scf per barrel of charge (355-5,333 std. m$^3$/m$^3$). Suitable hydrotreating conditions are generally within the broad ranges of hydrocracking conditions set out above.

The reaction zone effluent is normally removed from the catalyst bed, subjected to partial condensation and vapor-liquid separation and then fractionated to recover the various components thereof. The hydrogen, and if desired some or all of the unconverted heavier materials, are recycled to the reactor. Alternatively, a two-stage flow may be employed with the unconverted material being passed into a second reactor. Catalysts of the subject invention may be used in just one stage of such a process or may be used in both reactor stages.

Catalytic cracking processes are preferably carried out with the MAPSO-64 composition using feedstocks such as gas oils, heavy naphthas, deasphalted crude oil residua, etc. with gasoline being the principal desired product. Temperature conditions of 850° to 1100° F., LHSV values of 0.5 to 10 and pressure conditions of from about 0 to 50 psig are suitable.

Alkylation of aromatics usually involves reacting an aromatic ($C_2$ to $C_{12}$), especially benzene, with a monoolefin to produce a linear alkyl substituted aromatic. The process is carried out at an aromatic:olefin (e.g., benzene:olefin) ratio of between 5:1 and 30:1, a LHSV of about 0.3 to about 6 hr$^{-1}$, a temperature of about 100° to about 250° C. and pressures of about 200 to about 1000 psig. Further details on apparatus may be found in U.S. Pat. No. 4,870,222 which is incorporated by reference.

Alkylation of isoparaffins with olefins to produce alkylates suitable as motor fuel components is carried out at temperatures of −30° to 40° C., pressures from about atmospheric to about 6,894 kPa (1,000 psig) and a weight hourly space velocity (WHSV) of 0.1 to about 120. Details on paraffin alkylation may be found in U.S. Pat. No. 5,157,196 and U.S. Pat. No. 5,157,197, which are incorporated by reference.

The conversion of methanol to olefins is effected by contacting the methanol with the MAPSO-64 catalyst at conversion conditions, thereby forming the desired olefins. The methanol can be in the liquid or vapor phase with the vapor phase being preferred. Contacting the methanol with the MAPSO-64 catalyst can be done in a continuous mode or a batch mode with a continuous mode being preferred. The amount of time that the methanol is in contact with the MAPSO-64 catalyst must be sufficient to convert the methanol to the desired light olefin products. When the process is carried out in a batch process, the contact time varies from about 0.001 hrs to about 1 hr, and in another embodiment, from about 0.01 hr to about 1.0 hr. The longer contact times are used at lower temperatures while shorter times are used at higher temperatures. Further, when the process is carried out in a continuous mode, the Weight Hourly Space Velocity (WHSV) based on methanol can vary from about 1 hr$^{-1}$ to about 1000 hr$^{-1}$ and in another embodiment, from about 1 hr$^{-1}$ to about 100 hr$^{-1}$.

Generally, the process must be carried out at elevated temperatures in order to form light olefins at a fast enough rate. Thus, the process should be carried out at a temperature of about 300° C. to about 600° C., preferably from about 400° C. to about 550° C. and most preferably from about 450° C. to about 525° C. The process may be carried out over a wide range of pressure including autogenous pressure. Thus, the pressure can vary from about 0 kPa (0 psig) to about 1724 kPa (250 psig) and preferably from about 34 kPa (5 psig) to about 345 kPa (50 psig).

Optionally, the methanol feedstock may be diluted with an inert diluent in order to more efficiently convert the methanol to olefins. Examples of the diluents which may be used are helium, argon, nitrogen, carbon monoxide, carbon dioxide, hydrogen, steam, paraffinic hydrocarbons, e.g., methane, aromatic hydrocarbons, e.g., benzene, toluene and mixtures thereof. The amount of diluent used can vary considerably and is usually from about 5 to about 90 mole percent of the feedstock and preferably from about 25 to about 75 mole percent.

The actual configuration of the reaction zone may be any known catalyst reaction apparatus known in the art. Thus, a single reaction zone or a number of zones arranged in series or parallel may be used. In such reaction zones the methanol feedstock is flowed through a bed containing the MAPSO-64 catalyst. When multiple reaction zones are used, one or more MAPSO-64 catalysts may be used in series to produce the desired product mixture. Instead of a fixed bed, a dynamic bed system, e.g., fluidized or moving, may be used. Such a dynamic system would facilitate any regeneration of the MAPSO-64 catalyst that may be required. If regeneration is required, the MAPSO-64 catalyst can be continuously introduced as a moving bed to a regeneration zone where it can be regenerated by means such as oxidation in an oxygen containing atmosphere to remove carbonaceous materials.

The following examples are presented in illustration of this invention and are not intended as undue limitations on the generally broad scope of the invention as set out in the appended claims.

The structure of the MAPSO-64 compositions of this invention was determined by the analysis of x-ray powder patterns. The x-ray patterns presented in the following examples were obtained using standard x-ray powder diffraction techniques. The radiation source was a high-intensity, x-ray tube operated at 45 kV and 35 ma. The diffraction pattern from the copper K-alpha radiation was obtained by appropriate computer based techniques. Flat compressed powder samples were continuously scanned at 2° to 56° (2θ). Interplanar spacings (d) in Angstrom units were obtained from the position of the diffraction peaks expressed as θ where θ is the Bragg angle as observed from digitized data. Intensities were determined from the integrated area of diffraction peaks after subtracting background, "$I_o$" being the intensity of the strongest line or peak, and "I" being the intensity of each of the other peaks.

As will be understood by those skilled in the art the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline materials from each other and from the compositions of the prior art. In some of the x-ray patterns reported, the relative intensities of the d-spacings are indicated by the notations vs, s, m, and w which represent very strong, strong, medium, and weak, respectively. In terms of $100 \times I/I_o$, the above designations are defined as:

$$w=0-15; m=15-60; s=60-80 \text{ and } vs=80-100$$

In certain instances the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present.

In order to more fully illustrate the invention, the following examples are set forth. It is to be understood that the examples are only by way of illustration and are not intended as an undue limitation on the broad scope of the invention as set forth in the appended claims.

Example 1

A Teflon beaker was charged 100.00 g DEDMAOH (20%), which was then stirred with a high-speed mixer. Then 4.65 g Al(OH)$_3$ (78.1%) was added a bit at a time with stirring until the reaction mixture was nearly a clear solution. Next 5.94 g TEOS (98%) was added quickly via dropper. The reaction mixture was stirred for 1.5 hours to give the TEOS a chance to hydrolyze. The reaction mixture was then treated with 12.89 g H$_3$PO$_4$ (85%), added dropwise over a 15 minute period and allowed to stir for an additional 20 minutes, at which point the solution was clear. Separately, 20.5 g Zn(OAc)$_2$*2H$_2$O was dissolved in 10.00 g de-ionized water. This solution was added slowly, dropwise, and the reaction mixture remained a clear solution. The reaction mixture was stirred for an additional hour before it was distributed among 7 Teflon-lined autoclaves, and digested at autogenous pressures at various temperatures and time periods. The products were isolated and washed with de-ionized water by centrifugation. The products resulting from reaction mixtures digested at 150° C. for 55 and 152 hours and 175° C. for 55 hours were identified as MAPSO-64 by powder x-ray diffraction. Table 1 below shows representative diffraction lines for the 150° C./152 hour phase. Elemental analysis of this product had the elemental ratios C/N=6.38, N/Al=0.40, Zn/Al=0.97, P/Al=1.59, Si/Al=0.16, consistent with the stoichiometry DEDMA$_{0.40}$Zn$_{0.96}$AlP$_{1.59}$Si$_{0.16}$O$_{6.96}$.

TABLE 1

| 2-Θ | d(Å) | I/I$_0$(%) |
|---|---|---|
| 6.66 | 13.26 | vs |
| 7.60 | 11.63 | m |
| 13.22 | 6.69 | w |
| 13.36 | 6.62 | m |
| 14.80 | 5.98 | w |
| 15.40 | 5.75 | w |
| 16.66 | 5.32 | w |
| 18.84 | 4.71 | m |
| 20.12 | 4.41 | m |
| 20.26 | 4.38 | w |
| 20.35 | 4.36 | w |
| 21.32 | 4.16 | w |
| 23.93 | 3.72 | w |
| 24.16 | 3.68 | w |
| 24.34 | 3.65 | w |
| 26.64 | 3.34 | w |
| 26.92 | 3.31 | w |
| 27.48 | 3.24 | w |
| 27.72 | 3.22 | w |
| 28.54 | 3.12 | w |
| 28.68 | 3.11 | w |
| 29.88 | 2.99 | w |
| 30.10 | 2.97 | w |
| 30.80 | 2.90 | w |
| 33.64 | 2.66 | w |
| 33.90 | 2.64 | w |
| 35.44 | 2.53 | w |
| 36.48 | 2.46 | w |
| 38.19 | 2.35 | w |
| 43.50 | 2.08 | w |

Example 2

A Teflon beaker was charged with 100.00 g ETMAOH (20%) and placed under a high speed stirrer. With vigorous stirring, 5.27 g Al(OH)$_3$ (78.1%) slowly added and this dissolved readily. This was followed by the addition of 6.74 g TEOS (98%) in a single pour. After stirring for 30 minutes to hydrolyze the TEOS, 14.61 g H$_3$PO$_4$ (85%) was added dropwise. The result was a clear solution. Separately, 2.32 g Zn(OAc)$_2$*2H$_2$O was dissolved in 10.00 g de-ionized water. This solution was added dropwise to the reaction mixture which remained a clear solution. After further homogenization, the reaction mixture was distributed among 7 teflon-lined autoclaves and digested at autogenous pressure at various temperatures and time periods. The products were isolated and washed with de-ionized water by centrifugation. The product resulting from the 125° C./180 hour digestion was identified as MAPSO-64 as determined by powder x-ray diffraction. Table 2 below shows representative diffraction lines for this product.

TABLE 2

| 2-Θ | d(Å) | I/I$_0$(%) |
|---|---|---|
| 6.76 | 13.06 | m |
| 7.70 | 11.47 | vs |
| 13.30 | 6.65 | m |

TABLE 2-continued

| 2-Θ | d(Å) | I/I₀(%) |
|---|---|---|
| 13.45 | 6.58 | m |
| 14.90 | 5.94 | w |
| 15.40 | 5.75 | w |
| 15.50 | 5.71 | w |
| 18.92 | 4.69 | m |
| 20.21 | 4.39 | m |
| 20.32 | 4.37 | m |
| 21.42 | 4.15 | m |
| 24.05 | 3.70 | w |
| 24.22 | 3.67 | m |
| 24.43 | 3.64 | w |
| 26.72 | 3.33 | m |
| 27.52 | 3.24 | m |
| 27.80 | 3.21 | w |
| 28.62 | 3.12 | w |
| 28.75 | 3.10 | w |
| 29.98 | 2.98 | m |
| 30.19 | 2.96 | m |
| 30.94 | 2.89 | w |
| 31.19 | 2.87 | w |
| 33.72 | 2.66 | m |
| 34.02 | 2.63 | w |
| 35.52 | 2.53 | w |
| 36.54 | 2.46 | w |
| 38.30 | 2.35 | w |
| 43.48 | 2.08 | w |
| 49.28 | 1.85 | w |
| 49.93 | 1.82 | w |

Example 3

A Teflon beaker was charged with 130.00 g ETMAOH (20%) and 6.19 g colloidal silica (Ludox AS-40, 40% $SiO_2$) and stirred briefly before it was placed in a Teflon bottle and digested at 95° C. for 2 hours. The solution was cooled and 6.29 g $Al(OH)_3$ (85.1%) was added slowly with vigorous stirring. The reaction mixture was homogenized for 45 minutes post-addition and never clarified, remaining hazy. This was followed by the drop-wise addition of 19.00 g $H_3PO_4$ (85%). The resulting reaction mixture is only semi-transparent. Separately, 1.51 g $Zn(OAc)_2*2H_2O$ in 6.0 g de-ionized water. This solution was added to the vigorously stirred reaction mixture in a drop-wise fashion with the homogenous reaction mixture becoming more opaque during the addition. The reaction mixture was divided among 7 Teflon-lined autoclaves and digested at autogenous pressure at various temperatures and time periods. The products were isolated and washed with de-ionized water by centrifugation. The product resulting from the 150° C./47 hour digestion was identified as MAPSO-64 by powder x-ray diffraction, but the sample contained a slight MAPSO-59 impurity. Table 3 below shows the representative diffraction lines for the MAPSO-64 product.

TABLE 3

| 2-Θ | d(Å) | I/I₀(%) |
|---|---|---|
| 6.67 | 13.24 | m |
| 7.60 | 11.62 | vs |
| 8.98 | 9.84 | w* |
| 13.20 | 6.70 | m |
| 13.36 | 6.62 | m |
| 14.77 | 5.99 | w |
| 15.38 | 5.76 | m |
| 18.08 | 4.90 | w* |
| 18.84 | 4.71 | m |
| 20.14 | 4.41 | m |
| 20.76 | 4.28 | w* |
| 21.32 | 4.16 | m |
| 22.44 | 3.96 | w* |

TABLE 3-continued

| 2-Θ | d(Å) | I/I₀(%) |
|---|---|---|
| 23.96 | 3.71 | w |
| 24.16 | 3.68 | m |
| 24.34 | 3.65 | w |
| 26.60 | 3.35 | m |
| 27.46 | 3.25 | w |
| 27.70 | 3.22 | w |
| 28.55 | 3.12 | w |
| 28.70 | 3.11 | w |
| 29.90 | 2.99 | m |
| 30.12 | 2.96 | m |
| 30.86 | 2.90 | w |
| 31.16 | 2.87 | w |
| 33.66 | 2.66 | w |
| 33.93 | 2.64 | w |
| 35.44 | 2.53 | w |
| 36.52 | 2.46 | w |
| 38.24 | 2.35 | w |
| 43.40 | 2.08 | w |

*MAPSO-59 impurity

Example 4

A Teflon bottle was charged with 193.3 g DEDMAOH (20%) and 8.12 g colloidal silica (Ludox AS-40, 40% SiO2), sealed and placed in an oven at 100° C. for 1.5 hours. The resulting DEDMA silicate solution was placed in a Teflon beaker under a high speed stirrer. Then 8.37 g $Al(OH)_3$ (83.0%) was added with vigorous stirring. Next 24.95 g $H_3PO_4$ (85%) was added drop-wise and the reaction mixture further homogenized. Separately, 1.98 g $Zn(OAc)_2*2H_2O$ was dissolved in 13.29 g de-ionized water. This solution was added drop-wise to the reaction mixture, which was further homogenized for 30 minutes. The final reaction mixture was a transparent white suspension. A portion of the reaction mixture was placed in a Teflon-lined autoclave and digested at 125° C. for 161 hours. The product was isolated and washed with de-ionized water via centrifugation. The product was identified as MAPSO-64 by powder x-ray diffraction. Representative diffraction lines for the product are shown in Table 4 below.

TABLE 4

| 2-Θ | d(Å) | I/I₀(%) |
|---|---|---|
| 6.70 | 13.19 | m |
| 7.62 | 11.60 | vs |
| 10.13 | 8.73 | w |
| 13.20 | 6.70 | m |
| 13.39 | 6.61 | m |
| 14.84 | 5.97 | w |
| 15.44 | 5.74 | m |
| 16.66 | 5.32 | w |
| 18.86 | 4.70 | m |
| 20.18 | 4.40 | m |
| 21.34 | 4.16 | m |
| 23.98 | 3.71 | w |
| 24.18 | 3.68 | m |
| 24.34 | 3.65 | m |
| 26.64 | 3.34 | w |
| 26.98 | 3.30 | w |
| 27.46 | 3.25 | w |
| 27.72 | 3.22 | w |
| 28.54 | 3.12 | w |
| 28.71 | 3.11 | w |
| 29.90 | 2.99 | m |
| 30.18 | 2.96 | m |
| 30.82 | 2.90 | m |
| 33.66 | 2.66 | w |
| 33.99 | 2.64 | w |

TABLE 4-continued

| 2-Θ | d(Å) | I/I₀(%) |
|---|---|---|
| 35.46 | 2.53 | w |
| 36.42 | 2.47 | w |
| 36.56 | 2.46 | w |
| 38.26 | 2.35 | w |
| 39.07 | 2.30 | w |
| 39.82 | 2.26 | w |
| 40.39 | 2.23 | w |
| 43.42 | 2.08 | w |
| 43.65 | 2.07 | w |
| 49.88 | 1.83 | w |
| 55.69 | 1.65 | w |

Example 5

A Teflon beaker was charged with 130.00 g ETMAOH (20%) and 6.19 g colloidal silica (Ludox AS-40, 40% SiO$_2$), the mixture was stirred briefly, transferred to a Teflon bottle, and digested at 95° C. for 2 hours. The resulting ETMA silicate solution was placed in a beaker under a high speed stirrer and 6.29 g Al(OH)$_3$ (85.1%) was added slowly, resulting in a cloudy reaction mixture, even after 45 minutes of post addition homogenization. Next, 19.00 g H$_3$PO$_4$ (85%) was added intermittently in a drop-wise fashion. A semi-transparent reaction mixture results. Separately, 3.01 g Zn(OAc)$_2$*2H$_2$O was dissolved in 12.0 g de-ionized water. This solution was added intermittently in three different additions in a drop-wise fashion while the reaction mixture was vigorously stirred. The reaction mixture remained homogenous, but became more opaque. The reaction mixture was loaded into 7 Teflon-lined autoclaves and digested at autogenous pressure at various temperatures and time periods. The products were isolated and washed with de-ionized water by centrifugation. The product resulting from the 125° C./183 hour digestion was identified as MAPSO-64 by powder x-ray diffraction. The representative diffraction lines for this product are shown in Table 5 below.

TABLE 5

| 2-Θ | d(Å) | I/I₀(%) |
|---|---|---|
| 6.68 | 13.22 | m |
| 7.62 | 11.59 | vs |
| 13.22 | 6.69 | m |
| 13.38 | 6.61 | m |
| 14.83 | 5.97 | w |
| 15.41 | 5.75 | w |
| 18.86 | 4.70 | m |
| 20.14 | 4.41 | m |
| 20.26 | 4.38 | m |
| 21.36 | 4.16 | s |
| 23.98 | 3.71 | w |
| 24.15 | 3.68 | m |
| 24.36 | 3.65 | m |
| 26.68 | 3.34 | m |
| 27.48 | 3.24 | m |
| 27.74 | 3.21 | w |
| 28.55 | 3.12 | w |
| 28.72 | 3.11 | w |
| 29.92 | 2.98 | m |
| 30.14 | 2.96 | m |
| 30.86 | 2.90 | m |
| 33.70 | 2.66 | w |
| 33.97 | 2.64 | w |
| 35.48 | 2.53 | w |
| 36.50 | 2.46 | w |
| 38.26 | 2.35 | w |
| 40.43 | 2.23 | w |
| 43.50 | 2.08 | w |

What is claimed is:

1. A process for hydrocracking or hydrotreating comprising contacting a stream comprising at least one hydrocarbon with a catalyst at hydrocarbon conversion conditions to generate at least one converted product comprising hydrocracking or hydrotreating products, wherein the catalyst is a microporous crystalline MAPSO-64M material comprising a three-dimensional framework of EO$_2^-$, PO$_2^+$, [M$^{2+}$O$_2$]$^{2-}$ and SiO$_2$ tetrahedral units the composition given by the empirical formula:

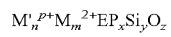

where M is at least one metal cation of valence +2 selected from the group consisting of Be$^{2+}$, Mg$^{2+}$, Zn$^{2+}$, Co$^{2+}$, Mn$^{2+}$, Fe$^{2+}$, Ni$^{2+}$, "m" is the mole ratio of M to E and varies from 0 to about 1.5, M' is selected from the group consisting of NH$_4^+$, H$^+$, alkali metals, alkaline earth metals, rare earth metals, and mixtures thereof, "n" is the mole ratio of M' to E and has a value of about 0.03 to about 2.0, "p" is the weighted average valence of M', E is an trivalent element selected from the group consisting of aluminum, gallium, iron, boron and mixtures thereof, "x" is mole ratio of P to E and varies from 0.5 to about 2.5, "y" is the mole ratio of Si to E and varies from 0.01 to about 1.0 and "z" is the mole ratio of O to E and has a value determined by the equation:

$$z=(p \cdot n+2 \cdot m+3+5 \cdot x+4 \cdot y)/2$$

and is characterized in that it has the x-ray diffraction pattern having at least the d-spacings and intensities set forth in Table A:

TABLE A

| 2Θ | d(Å) | I/I₀ |
|---|---|---|
| 6.81-6.61 | 12.98-13.34 | m-vs |
| 7.75-7.55 | 11.40-11.70 | m-vs |
| 13.36-13.14 | 6.62-6.73 | w-m |
| 13.51-13.32 | 6.55-6.64 | w-m |
| 14.98-14.68 | 5.91-6.03 | w |
| 15.51-15.34 | 5.71-5.77 | w-m |
| 18.99-18.79 | 4.67-4.72 | w-m |
| 20.26-20.07 | 4.38-4.42 | w-m |
| 21.50-21.24 | 4.13-4.18 | w-s |
| 24.10-23.84 | 3.69-3.73 | w-m |
| 24.30-24.03 | 3.66-3.70 | w-m |
| 24.57-24.23 | 3.62-3.67 | w-m |
| 26.83-26.51 | 3.32-3.36 | w-m |
| 27.59-27.42 | 3.23-3.25 | w-m |
| 27.86-27.59 | 3.20-3.23 | w |
| 28.68-28.49 | 3.11-3.13 | w |
| 28.87-28.59 | 3.09-3.12 | w |
| 30.06-29.76 | 2.97-3.00 | w-m |
| 30.27-29.96 | 2.95-2.98 | w-m |
| 31.03-30.70 | 2.88-2.91 | w-m |
| 33.80-33.54 | 2.65-2.67 | w-m |
| 34.06-33.80 | 2.63-2.65 | w |
| 35.60-35.31 | 2.52-2.54 | w-m |
| 36.65-36.34 | 2.45-2.47 | w |
| 38.44-38.10 | 2.34-2.36 | w | wherein the hydrocracking or hydrotreating process is operated at a temperature in the range of about 400° to about 1200° F. (204-649° C.) and a pressure in the range of atmospheric to about 3,500 psig (24,132 kPa g).

2. The process of claim 1 wherein the hydrocracking or hydrotreating is operated at a liquid hourly space velocities (LHSV) in the range of about 0.1 hr$^{-1}$ to 15 hr$^{-1}$.

3. The process of claim 1 wherein the hydrocracking or hydrotreating is operated at hydrogen circulation rates in the range of 1,000 to 50,000 standard cubic feet (scf) per barrel of charge (178-8,888 std. m$^3$/m$^3$).

4. The process of claim 1 further comprising removing an effluent comprising the at least one converted product, fractionating the effluent, and recovering at least one converted product.

5. The process of claim 4 further comprising, subjecting the effluent to partial condensation and vapor-liquid separation prior to fractionation.

6. The process of claim 4 further comprising recycling at least a portion of the effluent to the catalyst.

7. The process of claim 1 wherein the hydrocarbon conversion process comprises two stage operation and the catalyst is present in at least one of the two stages.

8. The process of claim 1 wherein the hydrocarbon conversion process is catalytic cracking operated at a temperature in the range of about 850° to about 1100° F., LHSV values of 0.5 to 10 and a pressure in the range of from about 0 to about 50 psig.

9. The process of claim 8 wherein the hydrocarbon stream is selected from the group consisting of gas oils, heavy naphthas, and deasphalted crude oil residua.

10. The process of claim 1 wherein the catalyst is located in one or more catalyst zones arranged in series or parallel configuration, and wherein the catalyst may be in fixed beds or fluidized beds.

11. The process of claim 1 further comprising regenerating the catalyst.

* * * * *